US00PP15253P2

(12) United States Plant Patent
Kordes

(10) Patent No.: US PP15,253 P2
(45) Date of Patent: Oct. 19, 2004

(54) SHRUB ROSE PLANT NAMED 'KORRAVRELI'

(50) Latin Name: *Rosa Hybrida*
Varietal Denomination: KORravreli

(75) Inventor: Wilhelm Kordes, Sparrieshoop (DE)

(73) Assignee: W. Kordes' Sohne Rosenschulen GmbH, Sparrieshop (DE)

( * ) Notice: Subject to any disclaimer, the term of this patent is extended or adjusted under 35 U.S.C. 154(b) by 0 days.

(21) Appl. No.: 10/728,005

(22) Filed: Dec. 3, 2003

(51) Int. Cl.[7] ..... A01H 5/00
(52) U.S. Cl. ..... Plt./102
(58) Field of Search ..... Plt./102, 105, 106, Plt./107, 147, 136

(56) References Cited

PUBLICATIONS

UPOV–ROM GTITM, Plant Variety Database, 2003/06, GTI Jouve Retrieval Software, Citation for *Rosa* 'Korravreli'.*

* cited by examiner

*Primary Examiner*—Anne Marie Grunberg
*Assistant Examiner*—June Hwu
(74) *Attorney, Agent, or Firm*—Klarquist Sparkman LLP

(57) ABSTRACT

Shrub rose plant having large red well formed flower with high petal count; shrubby, upright and spreading plant habit; resistance to rust and powdery mildew; and spice-like fragrance.

1 Drawing Sheet

Genus and species: *Rosa hybrida.*
Variety denomination: 'KORravreli'.

ORIGIN OF THE INVENTION

The present invention relates to a new and distinct variety of a shrub rose plant named 'KORravreli' which was originated by me by crossing the variety 'DELge' (Centenaire de Lourdes), (not patented), with the variety 'TANeitber' (Bernstein-Rose), (not patented).

BACKGROUND OF THE INVENTION

The primary objective of this breeding was to produce a new rose variety having the disease resistance and shrub habit of the female parent combined with the larger flower, petal count and fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large, red, well formed flower with high petal count;
2. Shrubby, upright and spreading plant habit;
3. Resistance to rust and powdery mildew;
4. Spice-like fragrance.

Asexual reproduction of this new variety by cuttings, as performed at Wasco, Calif. shows that the foregoing and all other characteristics and distinctions come true to form and are established and transmitted through succeeding propagations.

Comparison with Parents

The subject variety differs from female parent 'DELgel' (Centenaire de Lourdes) in flower color (rose-pink for 'DELge', apricot-pink for 'KORravreli'), petal count (10–15 versus 70–80) and from male parent 'TANeitber' (Bernstein-Rose) in flower color (yellow for 'DELge', apricot for 'KORravreli'), plant size (80 cm×60 cm versus 120 cm×90 cm).

Comparison with Similar Variety

The closest variety known to me is 'AUSgold' (Golden Celebration), U.S. Pat. No. 8,688. It differs from 'KORravreli' in flower color (apricot pink versus yellow), petal count (55 versus 70–80), and fragrance (old rose versus spice).

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:

*Seed parent.*—'DELge' (Centenaire de Lourdes). Not patented.

*Pollen parent.*—'TANeitber' (Bernstein-Rose). Not patented.

FLOWER

Observations made January to October 2003 from plants commencing from a dormant two year old bare root plant, grown in a garden environment at Somis, Calif.

Blooming Habit: Continuous.

Bud:

*Size.*—About 3 cm long and 2.5 cm in diameter when the petals start to unfurl.

*Form.*—The bud form is short, pointed ovoid.

*Color.*—When sepals first divide, but color is Red Group 42B. When half blown, the upper sides of the petals on the outer two thirds are Red Group 38D with the inner one-third of the petal Yellow Group 2D; the lower sides of the petals are Red Group 38A.

*Sepals.*—Color: Upper surface: Green Group 138B, but usually with an overlay of Greyed-Red Group 181B. Lower surface: Green Group 137A. Length: 25 mm. Width: 7 mm. Shape: Subulate. Surface texture: Upper surface: Canescent. Lower surface: Coriaceous. Margin: Ciliolate. There are three lightly appendaged sepals. There are two unappendaged sepals with hairy edges.

*Receptacle.*—Color: Yellow-Green Group 146C. Shape: Funnel. Size: Medium, about 5 mm long×8 mm wide. Surface: smooth.

*Peduncle.*—Length: Short, averaging about 35–40 mm. Surface: Glandular. Color: Yellow-Green Group 146C, often overlain with Greyed-Purple Group 184A. Strength: Bending, moderately strong Bloom:

*Size.*—Very large. Average open diameter is about 13–15 cm.

*Borne.*—In pyramidal clusters of three blooms.

*Stems.*—Strength: Strong. Average length is about 30–40 cm with a diameter of 4–5 mm.

*Form.*—When first open: Cupped. Permanence: Retains its form to the end, outer petal edges curl slightly.

*Petalage.*—Number of petals under normal conditions: 70–80.

*Color.*—The upper sides of the petals are Red Group 38D on the outer two thirds; inner third being Yellow Group 2D. The reverse sides of the petals are Red Group 38A. The base of each petal has a light yellow color spot 3 mm×3 mm, close to Yellow Group 2C. The major color on the upper side is Red Group 38D.

*Variegations.*—None.

*Discoloration.*—The general tonality at the end of the first day: Little change. At the end of the third day: Some fading on outer petals to Red Group 49D.

*Fragrance.*—Moderate, spicy.

Petals:

*Texture.*—Thick.

*Shape.*—Outer two or three rows; Round. Inner rows of petals: Deltoid.

*Size.*—40–50 mm in length×40–50 mm in width.

*Surface.*—Smooth.

*Margin.*—Entire.

*Apex shape.*—Obtuse.

*Base shape.*—Rounded.

*Form.*—Edges slightly quilled.

*Arrangement.*—Regularly arranged/shingle-like.

*Petaloids.*—Number: 5–15 Color: Upper Surface: Red Groups 38D. Lower Surface: Red Group 38B. Size: 6 mm in length×2 mm in diameter to 11 mm in length×4 mm in diameter. Shape: Subulate.

*Persistence.*—Petals drop off clearly before drying.

*Lastingness.*—On the plant: Long (about 6–7 days). As a cut flower: Long (about 7–8 days).

Reproductive Parts:

*Stamens.*—Number: 30–35. Length: 10–11 mm. Anthers: Length: 3 mm. Color: Yellow Group 3C. Filaments: Color: Yellow Group 3A. Length: 7–8 mm. Pollen: Color: Greyed-Orange Group 165C.

*Pistils.*—Number: 45–50. Length: 8–9 mm. Styles: Color: Red Group 47C. Length: 7–8 mm. Stigmas: Color: Orange-White Group 159C. Length: 1 mm.

*Hips.*—None observed.

PLANT

*Form.*—Shrub.

*Growth.*—Very vigorous, branching, sprawling.

*Age at maturity.*—2 years.

*Mature plant.*—Height: 120–130 cm. Width: 90–100 cm.

*Rootstock.*—Own roots.

Foliage: Number of leaflets on normal mid-stem leaves: 5 or 7.

*Size.*—Large. About 16 cm long×9 cm wide.

*Quantity.*—Abundant.

*Color.*—New foliage: Upper side: Greyed-Purple Group 185A. Lower side: Greyed-Purple Group 184A. Old foliage: Upper side: Green Group 139A. Lower side: Green Group 137C.

Leaflets:

*Size.*—About 55–60 mm long×35–40 mm wide.

*Shape.*—Pointed oval.

*Base shape.*—Oblique.

*Apex shape.*—Acuminate.

*Texture.*—Leathery.

*Edge.*—Serrated.

*Serrations.*—Single.

*Petiole.*—Color: Yellow-Green Group 147B.

*Petiole rachis.*—Color: Yellow-Green Group 146B. Length: 120 mm. Diameter. 2 mm. Underside: Rough with prickles. Shape: Adnate.

*Auricles.*—None.

*Stipules.*—Length: 15–17 mm, serrated. Width: 3 mm. Surface Texture: Glabrous. Shape: Adnate. Color: Green Group 137A.

*Disease resistance.*—Resistant to mildew and rust and susceptible to blackspot under normal growing conditions.

*Pest resistance.*—None noted.

*Vein color.*—Green Group 137D.

*Venation pattern.*—Recticulate.

Wood:

*New wood.*—Color: Greyed Purple Group 185A. Bark: Smooth.

*Old wood.*—Color: Green Group 146B. Bark: Smooth.

Prickles:

*Quantity.*—On main canes from base: Ordinary. On laterals from main canes: Ordinary.

*Form.*—Hooked downward.

*Length.*—6–7 mm.

*Color when young.*—Greyed Purple Group 185A.

*Color when mature.*—Greyed-Yellow Group 161D.

Small Prickles:

*Quantity.*—On main stalks: None. On laterals: None.

Winter Hardiness: Hardy to Zone 5.

I claim:

1. A new and distinct variety of rose plant of the shrub class, substantially as herein shown and described, characterized particularly by large red well formed flower with high petal count; shrubby, upright and spreading plant habit; resistance to rust and powdery mildew; and spice-like fragrance.

* * * * *

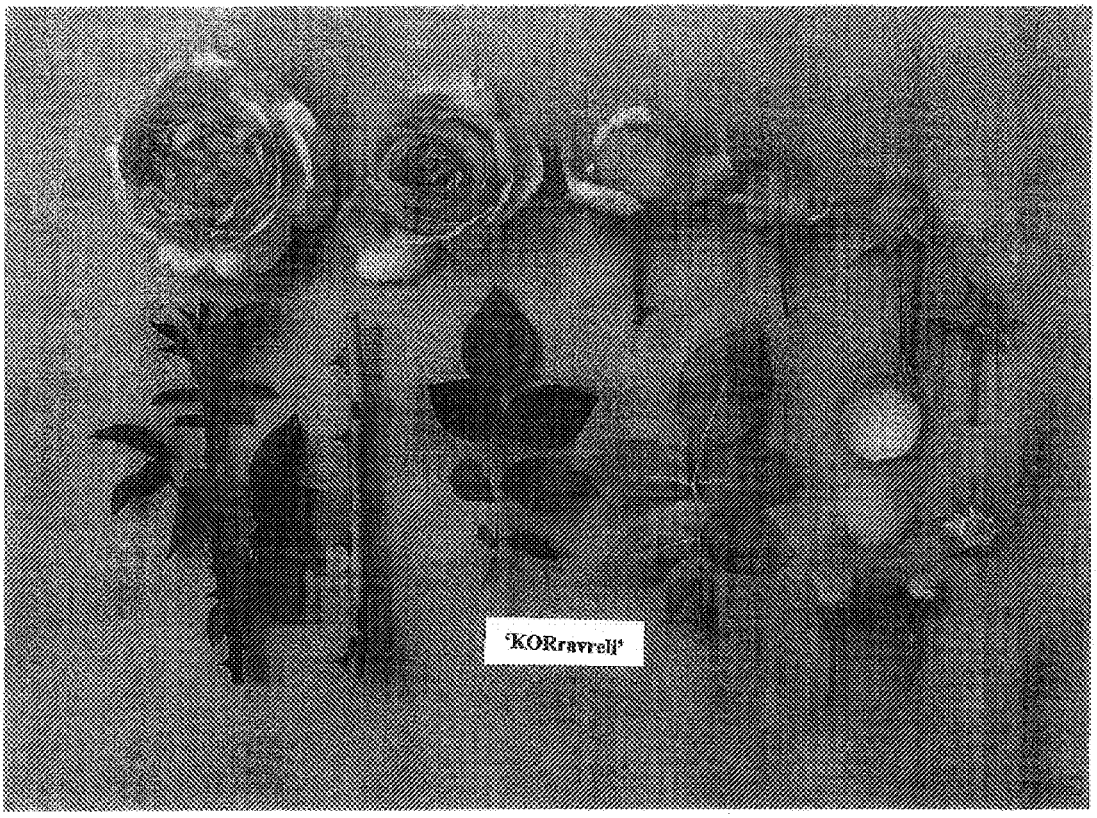
'KORravrell'